United States Patent [19]

Ho et al.

[11] 4,296,038
[45] Oct. 20, 1981

[54] PREPARATION OF (−)-DIHYDROCHRYSANTHEMOLACTONE

[75] Inventors: T. L. Ho; Zia U. Din, both of Jacksonville, Fla.

[73] Assignee: SCM Corporation, New York, N.Y.

[21] Appl. No.: 143,299

[22] Filed: Apr. 24, 1980

[51] Int. Cl.$^3$ ............................................. C07D 311/94
[52] U.S. Cl. ................................ 260/343.21; 568/819
[58] Field of Search ..................................... 260/343.21

[56] References Cited

U.S. PATENT DOCUMENTS

| | | | |
|---|---|---|---|
| 3,527,769 | 9/1970 | Matsui et al. | 260/343.21 |
| 3,565,915 | 2/1971 | Matsui et al. | 260/343.21 |
| 4,132,717 | 1/1979 | Roman | 260/343.21 |

OTHER PUBLICATIONS

Sobti et al., Tetrahedron vol. 30, pp. 2927–2929, 1974.
Hajime et al., Agr. Bio. Chem. 40 (I), 169–174, 1976.
House, Modern Synthetic Reactions pp. 296–297.
Widmark, Arkiv for Kemi Band 11, nr 20, 195(1957).
Fieser & Fieser Reagents for Organic Synthesis pp. 682–684.
Matsui et al., Agr. Biol. Chem., vol. 31, No. 1 pp. 33–39, 1967.
Matsui et al., Agr. Biol. Chem. vol. 29, No. 8 pp. 784–786, 1965.

Primary Examiner—Henry R. Jiles
Assistant Examiner—Jane T. Fan
Attorney, Agent, or Firm—Robert A. Sturges; Merton H. Douthitt

[57] ABSTRACT

A four-step process for producing (−)-dihydrochrysanthemolactone from 2-caren-4-one is disclosed. The four steps in order are methylating 2-caren-4-one, oxidizing, methylating the tautomeric mixture resulting from the oxidation, and finally lactonizing the single hydroxy acid resulting from the second methylation. Additionally, three novel intermediate compounds that are produced by the steps in the process are disclosed.

5 Claims, No Drawings

PREPARATION OF (−)-DIHYDROCHRYSANTHEMOLACTONE

BACKGROUND OF THE INVENTION

The present invention relates to a process for producting (-)-dihydrochrysanthemolactone from 2-caren-4-one. The 2-caren-4-one is treated in succession with a methylating agent, an oxidizing agent, a methylating agent again, and finally a lactonizing agent. This invention also relates to the reaction intermediate compounds resulting from such treatment of 2-caren-4-one. The lactone so produced has been found to be a precursor for (+)-trans-chrysanthemic acid, which in itself is useful in the preparation of many synthetic pyrethroid insecticides.

The previously proposed route for synthesizing dihydrochrysanthemolactone is described in U.S. Pat. No. 3,565,915. However, the starting material differs in that the reference proposes beginning the synthesis with optically active 2,2-dimethyl-3-cis-(2'-oxopropyl) cyclopropyl-1-acetaldehyde. Additionally, during the synthesis, the compound is converted into optically active cis-homocaronic acid and then to optically active cis-homocaronic acid anhydride. However, a Grignard reagent is then used to convert the cis-homocaronic anhydride to the desired optically active dihydrochrysanthemolactone.

One advantage of the present invention is that it begins the synthesis of the desired product with 2-caren-4-one. This product is readily obtainable from (+)-3-carene which is available in commercial quantities. Additionally, only the desired optically active (−)-dihydrochrysanthemolactone is produced.

SUMMARY OF THE INVENTION

One aspect of this invention is a process for producing (−)-dihydrochrysanthemolactone from 2-caren-4-one wherein the 2-caren-4-one is first methylated to give the compound 4-methyl-2-caren-4-ol. This new reaction intermediate compound is then oxidized to produce a tautomeric mixture of cis-2,2-dimethyl-3-(2'-oxopropyl) cyclopropane-carboxylic acid and cis-2-oxo-3-oxa-4,7,7-trimethylbicyclo [4.1.0] heptan-4-ol. This tautomeric mixture is treated with a methylating agent, usually a methyl Grignard reagent, which yields a hydroxy acid upon acidification. Lactonization of the hydroxy acid to produce the desired (−)-dihydrochrysanthemolactone is accomplished by dehydration.

Other aspects of this invention include the novel reaction intermediate compounds of 4-methyl-2-caren-4-ol, cis2,2-dimethyl-3-(2°-oxopropyl) cyclopropane-carboxylic acid, and cis-2-oxo-3-oxa-4,7,7-trimethyl-bicyclo [4.1.0] heptan-4-ol.

DETAILED DESCRIPTION OF THE INVENTION

The present invention is conveniently illustrated by starting with the compound 2-caren-4-one. This compound can be obtained from the abundant and optically pure (+)-3-carene by methods known to those skilled in the art. The process basically consists of a four-step treatment of 2-caren-4-one to obtain the desired lactone. The first step is methylating the 2-caren-4-one to obtain a tertiary alcohol. The alcohol is oxidized in the next step which produces a tautomeric mixture. The third step consists of methylating this tautomeric mixture to obtain a hydroxy acid. The hydroxy acid is lactonized by dehydration in the final step. Throughout the four-step process, the stereochemistry of the compounds remains unchanged. The chiral centers at carbon atoms one and six of 2-caren-4-one are unaffected by the above steps.

The reaction intermediate compounds that are novel include the 4-methyl-2-caren-4-ol that is produced after treating 2caren-4-one with methyl lithium. The tautomeric mixture also contains novel compounds. The keto-acid component is cis-2,2-dimethyl-3-(2'-oxopropyl) cyclopropane-carboxylic acid. The other component of the tautomeric mixture is the lactol, a novel compound designated as cis-2-oxo-3-oxa-4,7,7-trimethylbicyclo [4.1.0] heptan-4-ol.

The ketone reactant, 2-caren-4-one obtained by known methods from (+)-3-carene, is methylated most commonly with methyl lithium in the first step of the four-step process. The reaction is begun at cool temperatures, 0° C. and below. The low temperatures give better control of the reaction. Throughout the reaction, the temperature is allowed to climb to room temperature. The reaction lasts approximately two hours. The reaction is quenched with water or similar substances such as lower alkanols. Extraction with pentane or other similar hydrocarbon solvents provides the tertiary alcohol of the following structure:

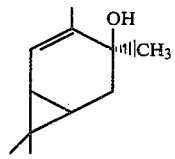

Oftentimes the extract containing the methylcarenol is treated again with methyl lithium and the same extraction procedure is followed to get a higher yield from the starting carenone. Yields as high as 92% methylcarenol can be so obtained. Other well-known methylating agents such as methyl magnesium halides can be used, and the desired temperature of reaction will depend upon the specific methylating agent used.

A second step of the inventive process involves oxidizing the resulting alcohol to give a keto-acid/lactol tautomeric mixture. The most convenient method for carrying out this step is ozonizing the alcohol produced in the first step, followed by an oxidative work-up removing two carbon atoms which leaves the two nine-carbon tautomeric compounds. Ozonization is accomplished by bubbling an ozone-oxygen mixture through the tertiary alcohol solution at a temperature, varying from −80° C. to +25° C., preferably around −78° C. The oxidative work-up is accomplished by the addition of hydrogen peroxide and later addition of sodium hydroxide in water. Following extraction with a hydrocarbon solvent to remove impurities, the aqueous phase is acidified with dilute hydrochloric acid, or other similar acids. During this acidification, the keto-acid is partially lactonized to produce the tautomeric mixture. The ratio of the tautomers varies with the reaction conditions. The tautomeric compounds have the following structure:

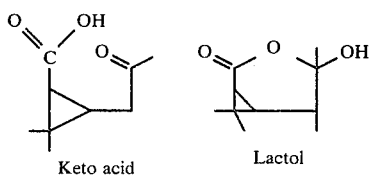

Keto acid       Lactol

The third step of preparing the (−)-dihydrochrysanthemolactone is again a methylating step. The most common methylating agent used is a methyl Grignard reagent. A particularly preferred methylating agent is methyl magnesium iodide. The reaction proceeds forward by the following mechanism:

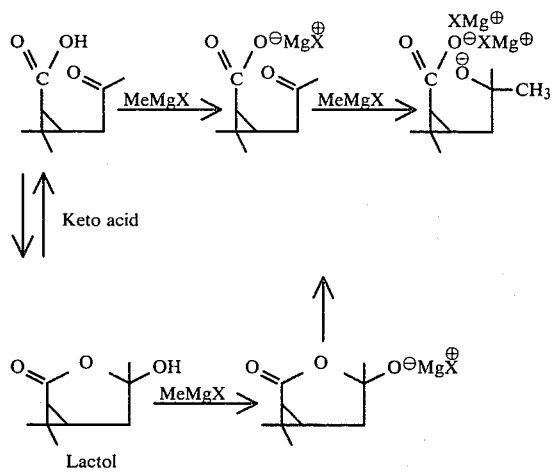

As illustrated above, the tautomeric mixture under the influence of the methylating Grignard reagent, shifts the equilibrium to the structure resulting from the reaction of the Grignard reagent with the keto acid. The lactol structure opens up under the influence of the Grignard reagent to give the salt of the keto acid. The Grignard reagent then adds the methyl group to the keto group. Subsequent to the refluxing of the tautomeric mixture with the Grignard reagent, the reaction is quenched with diluted acid. Preferably, this acid is dilute hydrochloric acid. The recovered product is a hydroxy acid of the following structure:

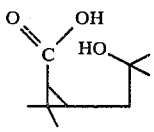

The final step in the process is to lactonize the hydroxy acid by dehydration. Preferably, this dehydration is accomplished by refluxing the recovered hydroxy acid in toluene containing p-toluene sulfonic acid. The reaction mixture is then washed with sodium carbonate solution. After evaporation of the organic phase, dihydrochrysanthemolactone is recovered. However, the sodium carbonate wash often has unlactonized hydroxy acid. This unconverted hydroxy acid can be recovered and recycled through the p-toluene-sulfonic acid refluxing solution to bring about a higher conversion.

The starting material 2-caren-4-one can be produced from commercially available, optically pure (+)-3-carene. The (+)-3-carene is treated with nitrosyl chloride followed by the addition of powdered sodium carbonate. The resulting 2-caren-4-one oxime is then treated with sodium bisulfite in aqueous ethanol to yield 2-caren-4-one, the desired starting product for the inventive process.

The following examples are intended to illustrate the invention and should not be construed as limiting the claims. The indicated temperatures are in degrees Celsius.

EXAMPLE 1

To prepare the starting reactant for the present invention, 67 gms of nitrosyl chloride gas were added into a stirred liquid of 152 gms of 3-carene during a two-hour period. At this stage the reaction mixture had become a thick syrup. The syrup was allowed to stand at 0° C. for 1 hour. To the syrup were added 200 mls of anhydrous isopropanol and 120 gms of powdered sodium carbonate. The stirring was resumed and the reaction mixture heated gently to reflux and allowed to reflux for two hours. Water was added after the reaction mixture had cooled to room temperature. The water dissolved all the salt and the reaction mixture was then extracted with diethyl ether. Removal of the ether gave 178 gms of residue which was stripped at a pressure of 0.4 mm and a temperature of 100°–105° C. The distillate was 83.1% 2-caren-4-one oxime weighing 127 gms. This represents a theoretical yield based upon 3-carene used of 68%.

The 127 gms of 2-caren-4-one oxime were mixed with 233 gms of sodium bisulfite and 1500 mls of 50% aqueous ethanol. This mixture was heated and allowed to reflux for 3.5 hours. Diluted acid, made by dissolving 385 mls of concentrated hydrochloric acid in 1500 mls of water, was added after the reaction mixture cooled to room temperature. Following this, 1000 mls of methylene chloride were added. This new reaction mixture was refluxed at 40° C. for 16 hours. The organic portion was separated and the solvent removed to yield 51 gms of product containing 63% carenone. The aqueous portion was mixed then with 1000 mls methylene chloride and the reaction mixture again refluxed for 18 hours. The organic portion was again separated and solvent removed to give an additional 14.3 gms of product containing 79% carenone. The aqueous portion left after the second reaction was mixed with 1000 mls methylene chloride and the reaction mixture refluxed for a final 12 hours. The organic portion was separated and solvent removed to yield a final 8.3 gms of product which contained 72% carenone. The total theoretical yield of carenone based on carenone oxime was 58%.

In undertaking this preparaton care should be taken due to the toxicity and corrosive character of nitrosyl chloride and due to the fact that oximes and ther intermediate nitroso compounds are known to decompose violently under certain conditions. All operations should be carried out in a well-shielded and well-ventilated work space.

EXAMPLE 2

The reaction product from Example 1,2-caren-4-one, 1.0 g dissolved in 10 mls of ether, was added to a stirred solution of 15 mls of 1.4 M methyl lithium. The reaction temperature was maintained at about −15° C. during the addition and was then allowed to come to room temperature and stirred for two hours. After two hours, the reaction was quenched with water and the product extracted with pentane. The solvent was removed to give 1.1 gm of reaction product which contained 60% of the tertiary alcohol, 4-methyl-2-caren-4-ol. The recovered product proved to contain 30% unconverted 2-caren-4-one.

The recovered product was again treated with 10 mls of methyl lithium as described above in this example. The final product was 0.8 gms which consisted of 92% methylcarenol and 8% starting reactant, carenone.

EXAMPLE 3

A solution of 2.2 gms of the product from Example 2, methylcarenol, in 50 mls of absolute methanol was ozonized at a temperature of $-78°$ C. by bubbling in a ozone-oxygen mixture. The reaction was concluded when an excess of ozone was detected in the reaction mixture. Next, the reaction mixture was stirred, 15 mls of water added, followed by the addition of 3 mls of 50% hydrogen peroxide. The mixture was stirred at room temperature for five hours. Sodium hydroxide, 3 gms in 6 mls of water, was added to the solution previously cooled by ice to a temperature of 0° C. This reaction mixture was then stirred at room temperature for 18 hours. The methanol solvent was removed in a rotary evaporator at 30°-50° C. The residue was dissolved in water and then extracted with pentane to remove nonacidic material. This aqueous solution was acidified with dilute hydrochloric acid and extracted with ether. Following evaporation of the ether, 2 gms of keto acid were obtained. This represents an 89% theoretical yield. The keto acid, however, provided to have been partially lactonized during the acid work-up.

EXAMPLE 4

From the material produced in Example 3, 2 gms of the tautomeric mixture of keto acid and lactol were dissolved in 50 mls of diethyl ether. A Grignard reagent previously prepared from 0.85 gms magnesium, 5.5 gms methyl iodide, and 50 mls ether was next added to the dissolved tautomeric mixture. This reaction mixture of product and Grignard reagent was refluxed for two hours and then quenched with diluted hydrochloric acid. Following removal of the solvent, 1.9 gms of recovered product consisted of lactone and hydroxy acid. The acid was separated and refluxed in 30 mls of toluene containing 30 mgs of p-toluene-sulfonic acid. The refluxing was carried on for one hour. After cooling, the reaction mixture was washed with sodium carbonate solution. Following removal of solvent, 0.6 gms of the desired $(-)$-dihydrochrysanthemolactone was recovered. The sodium carbonate wash proved to have 0.6 gms of the hydroxy acid for further processing

What is claimed is:

1. A process for producing $(-)$-dihydrochrysanthemolactone from 2-caren-4-one comprising:
    methylating said 2-caren-4-one with a methylating agent selected from methyl lithium and methyl magnesium halide to produce 4-methyl-2-caren-4-ol;
    oxidizing said 4-methyl-2-caren-4-ol with ozone followed by cleaving at the double bond with removal of 2 carbon atoms to produce a tautomeric mixture of cis-2,2-dimethyl-3(2'-oxopropyl) cyclopropane-carboxylic acid and cis-2-oxo-3-oxa-4,7,7-trimethylbicyclo [4.1.0] heptan-4-ol;
    methylating with a methylating agent selected from methyl lithium and methyl magnesium halide said tautomeric mixture to produce a single compound that upon acidification forms a hydroxy acid; and
    lactonizing said hydroxy acid by dehydration to produce said $(-)$-dihydrochrysanthemolactone.

2. The process of claim 1 wherein said 2-caren-4-one is methylated with methyl lithium.

3. The process of claim 1 wherein said 4-methyl-2-caren-4-ol is oxidized by ozonization followed by treatment with first hydrogen peroxide and then sodium hydroxide.

4. The process of claim 1 wherein said methyl Grignard reagent is methyl magnesium iodide.

5. The process of claim 1 wherein said 2-caren-4-one is produced from $(+)$-3-carene by reacting $(+)$-3-carene with nitrosyl chloride, followed by treatment with sodium carbonate to produce 2-caren-4-one oxime, which is deoximated by sodium bisulfite in aqueous ethanol to produce said 2-caren-4-one.

* * * * *